United States Patent
Zhou et al.

(10) Patent No.: US 9,757,456 B2
(45) Date of Patent: Sep. 12, 2017

(54) SUPER-SATURATING DELIVERY VEHICLES FOR POORLY WATER-SOLUBLE PHARMACEUTICAL AND COSMETIC ACTIVE INGREDIENTS AND SUPPRESSION OF CRYSTALLIZATION OF PHARMACEUTICAL ACTIVE INGREDIENTS

(75) Inventors: Chunfang Zhou, Stockholm (SE); Xin Xia, Bromma (SE); Alfonso E. Garcia-Bennett, Stockholm (SE)

(73) Assignee: Nanologica AB, Stockholm (SE)

( * ) Notice: Subject to any disclaimer, the term of this patent is extended or adjusted under 35 U.S.C. 154(b) by 19 days.

(21) Appl. No.: 13/823,334

(22) PCT Filed: Sep. 14, 2011

(86) PCT No.: PCT/EP2011/065959
§ 371 (c)(1),
(2), (4) Date: Mar. 14, 2013

(87) PCT Pub. No.: WO2012/035074
PCT Pub. Date: Mar. 22, 2012

(65) Prior Publication Data
US 2013/0171223 A1 Jul. 4, 2013

Related U.S. Application Data

(60) Provisional application No. 61/382,653, filed on Sep. 14, 2010.

(51) Int. Cl.
A61K 8/67 (2006.01)
A61K 9/51 (2006.01)
A61Q 19/00 (2006.01)
A61K 45/06 (2006.01)
(Continued)

(52) U.S. Cl.
CPC ............ *A61K 45/06* (2013.01); *A61K 8/0279* (2013.01); *A61K 8/67* (2013.01); *A61K 9/143* (2013.01);
(Continued)

(58) Field of Classification Search
CPC .............. A61K 9/143; A61K 2800/413; A61K 8/0279; A61K 8/67; A61K 9/51; A61Q 19/00
See application file for complete search history.

(56) References Cited

U.S. PATENT DOCUMENTS

2007/0275068 A1* 11/2007 Martens ............... A61K 9/1611
424/484
2009/0005384 A1 1/2009 Miura et al.
(Continued)

FOREIGN PATENT DOCUMENTS

JP 2010-509404 A 3/2010
WO WO-2006/080312 A1 8/2006
(Continued)

OTHER PUBLICATIONS

Slowing et al. (JACS 2006; 128:14792-14793).*
(Continued)

*Primary Examiner* — Ernst V Arnold
(74) *Attorney, Agent, or Firm* — Kim Winston LLP

(57) ABSTRACT

A pharmaceutical or cosmetic composition, comprising a substantially poorly water-soluble pharmaceutical active ingredient; and a nanoporous folic acid material, wherein the active pharmaceutical ingredient is incorporated inside the nanoporous channels of the particles.

20 Claims, 8 Drawing Sheets

(51) Int. Cl.
   *A61K 9/14* (2006.01)
   *A61K 31/4439* (2006.01)
   *A61K 8/02* (2006.01)
   *A61K 31/07* (2006.01)
   *A61K 31/496* (2006.01)
   *A61K 31/506* (2006.01)
   *A61K 38/05* (2006.01)

(52) U.S. Cl.
   CPC .......... *A61K 31/07* (2013.01); *A61K 31/4439* (2013.01); *A61K 31/496* (2013.01); *A61K 31/506* (2013.01); *A61K 38/05* (2013.01); *A61Q 19/00* (2013.01); *A61K 2800/10* (2013.01); *A61K 2800/413* (2013.01)

(56) References Cited

U.S. PATENT DOCUMENTS

2009/0192205 A1      7/2009  Augustijns
2010/0255103 A1*    10/2010  Liong et al. .................. 424/489

FOREIGN PATENT DOCUMENTS

| WO | WO-2007/108016 A1 | 9/2007 |
| WO | WO-2009/078924 A2 | 6/2009 |
| WO | WO-2009/088250 A2 | 7/2009 |
| WO | WO-2009/088553 A1 | 7/2009 |
| WO | 2009101110 | 8/2009 |
| WO | WO 2009101110 * | 8/2009 ............... A61K 9/14 |
| WO | WO-2009/118356 A2 | 10/2009 |
| WO | WO-2009/133100 A2 | 11/2009 |
| WO | WO-2010/050897 A1 | 5/2010 |

OTHER PUBLICATIONS

Monini et al. (Nature Reviews 2004; 4:861-875).*
Fukushima et al. (Biol Pharm Bull 2007; 30(4):733-738) p. 733; 1 page.*
Pyrko et al. (Cancer Res 2007;67(22):10920-8).*
Slowing et al. (Advanced Drug Delivery Reviews. 2008;60:1278-1288).*
Database Registry 113299-40-4, entered STN Mar. 12, 1988.
Database Registry 90357-06-5, entered STN Nov. 16, 1984.
Office Action for Japanese Patent Application No. 2013-528659, dated Mar. 23, 2016.
Office Action for Russian Patent Application No. 2013114252/15(021202), dated Jan. 11, 2016.
Office Action for Australian Patent Application No. 2011303849, dated May 13, 2016.

* cited by examiner

SUPER-SATURATING DELIVERY VEHICLES FOR POORLY WATER-SOLUBLE PHARMACEUTICAL AND COSMETIC ACTIVE INGREDIENTS AND SUPPRESSION OF CRYSTALLIZATION OF PHARMACEUTICAL ACTIVE INGREDIENTS

CROSS REFERENCE TO RELATED APPLICATIONS

This application is a National Phase filing under 35 U.S.C. §371 of PCT/EP2011/065959 filed on Sep. 14, 2011; and this application claims priority to U.S. Provisional Application No. 61/382,653 filed on Sep. 14, 2010 under 35 U.S.C. §119; the entire contents of all are hereby incorporated by reference.

FIELD OF THE INVENTION

The present invention relates to a super-saturating drug delivery system which comprises nanoporous materials and poorly water-soluble bioactive pharmaceutical compounds, capable of functioning even in the presence of proton pump inhibitors. Wet impregnation techniques, rotary evaporation techniques, co-spray drying technique or freeze-drying techniques can be applied to prepare the super-saturating delivery system. The mechanism of enhancement of dissolution is based on nano-confinement of the poorly soluble pharmaceutical active material within an ordered porous material via suppression of crystallization.

BACKGROUND OF THE INVENTION

More than one third of the drugs listed in the US Pharmacopoeia and up to 40% new chemical entities discovered by pharmaceutical industry are poorly soluble or lipophilic compounds. The solubility of active pharmaceutical ingredients (APIs) is one of the most challenging issues in the improvement of many existing pharmaceutical formulations or the development of new chemical entities for commercialization, because the maximum achievable intraluminal drug concentration will limit the drug adsorption and bioavailability. Furthermore, improvements in bioavailability of APIs can yield to reduction in toxic secondary effects due to the use of less active, improvements in patient comfort due to the possibility of administering drugs without decreases in gastrointestinal pH, and improvements in patient compliance through a reduction of the number of doses required to achieve an adequate therapeutic level of the API. Therefore, the configuration of supersaturating drug delivery systems is a promising concept to obtain adequate oral bioavailability and improve overall pharmacokinetic properties. Additionally reduction in compound dose through better pharmacokinetic properties directly yields a reduction in costs of treatment.

Much effort has been made to enhance the solubility of the poorly soluble drugs to increase the adsorption and bioavailability. One most common method is to reduce the drug particle size to increase surface area and curvature of particles which may improve the solubility and bioavailability of the drugs. The use of nanoparticles may further enhance the capacity to generate supersaturation [see: Matteucci M E, et al., Design of potent amorphous drug nanoparticles for rapid generation of highly supersaturated media. Mol Pharm 4:782-793. (2007); Overhoff K A, et al. Effect of stabilizer on the maximum degree and extent of supersaturation and oral absorption of tacrolimus made by ultra-rapid freezing. Pharm Res 25:167-175. (2008)]. However, the nanoparticles with high surface energy are easily aggregated, more costly than porous particles described in the present invention and may possess additional toxicological profiles.

The amorphous form of a drug has the highest apparent solubility, so amorphous-based dosage forms are a popular formulation strategy for poorly water-soluble drugs. Spray-drying of drug compounds has been somewhat successful in processing amorphous formulations of drug compounds. However, amorphous drugs are thermodynamically unstable and often lead to re-crystallization in the presence of small amounts of moisture. It is a major issue to avoid recrystallization during storage. Scientific and economic efforts have been made to avoid recrystallization of the drugs adding to the overall cost of treatments.

One or more polymers (e.g., polyvinylpyrrolidone (PVP), polyethyleneglycols (PEG), polymethacrylates, cellulose derivatives, inulin, etc.) and/or (polymeric) surfactants (e.g., Muted 1 SP1, Gelucire1, poloxamer 407, etc.) have been used to disperse amorphous drug particles [see: Serajuddin A T. Solid dispersion of poorly water-soluble drugs: Early promises, subsequent problems, and recent breakthroughs. J Pharm Sci 88:1058-1066; Leuner C, Dressman J. Improving drug solubility for oral delivery using solid dispersions. Eur J Pharm Biopharm 50:47-60. (2000); Vasconcelos T, et al. Solid dispersions as strategy to improve oral bioavailability of poor water soluble drugs. Drug Discovery Today 12:1068-1075 (2007)]. However, the incorporation of surfactants in formulation of poorly water-soluble drugs may cause irritation and side effects after oral administration in some cases, and they are liable to additional stability issues.

Recently, ordered nano (meso-)porous materials (e.g. silica) have been studied as carrier for the delivery of poorly water-soluble drugs [see: Salonen J, et al. Mesoporous silicon microparticles for oral drug delivery: Loading and release of five model drugs. J Control Release 108:362-374 (2005); Kaukonen A M, et al. Enhanced in vitro permeation of furosemide loaded into thermally carbonized mesoporous silicon (TCPSi) microparticles. Eur Pharm Biopharm 66:348-356 (2007); Shen S. C. Mesoporous materials excipients for poorly aqueous soluble ingredients, International Publication Number WO 2010/050897 A1]. Ordered nanoporous materials exhibits a 2-dimensionally or 3-dimensional ordered array of cylindrical or cage type pores (in the range of 2-50 nm) separated by thin silica walls. Bioactive drugs can be molecularly dispersed in these pores up to a certain loading (ca. 10-50% by weight). The influx diffusion of water to the pore surfaces provides for a rapid release of poorly water-soluble drugs if the drug compound is loaded in an amorphous state. It has been shown that the release of the weak base itraconazole from mesoporous materials gave rise to supersaturation in simulated gastric fluid; a subsequent pH shift to simulated intestinal fluid caused only limited precipitation and supersaturated concentrations were maintained for at least 4 h [see: Mellaerts R, et al. Enhanced release of itraconazole from ordered mesoporous SBA-15 silica materials. Chem Commun 13:1375-1377 (2007); Mellaerts R, et al. Ordered mesoporous silica induces pH-independent supersaturation of the basic low solubility compound itraconazole resulting in enhanced transepithelial transport. Int J Pharm 357:169-179 (2008); Mellaerts R, et al. Increasing the oral bioavailability of the poorly water soluble drug itraconazole with ordered mesoporous silica. Eur J Pharm Biopharm 69:223-230 (2008)].

Ordered nanoporous materials have been attracting much attention because of the regular and adjustable pore size, different pore structures, high surface area and pore volume, high concentrations of silanol groups which make the channels like wet environment. Much work has been made to enhance the solubility of poorly water-soluble drugs on SBA-15 with the bigger pore size. Herein the present invention discloses methods that provide for enhancements in poorly water-soluble drugs loaded in the mesoporous material with the smaller pore size showing higher apparent solubility, where additionally 2d-hexagonal pore structure show improvements over 3d-cubic pore structures. In addition, the super-saturating state produced from the nanoporous materials with smaller pore size could maintain longer time than the samples with bigger pore size. Therefore, it is necessary to apply the mesoporous materials with the smaller pore size and 2-D pore structure to deliver poorly water-soluble drugs.

Recently, one mesoporous materials named nanoporous folic acid-templated materials (NFM-1) have been developed by using the folic acid as template [see: Garcia-Bennett A. E. Method for manufacturing mesoporous, materials so produced and use of mesoporous materials; International Publication Number WO 2009/101110 A2]. These materials have the 2-D hexagonal pore structure with the pore size of a range between 1.8 and 3.5 nm and varied morphologies. Especially important, we show that through the present invention they show faster dissolution rates and higher apparent solubility than the samples with the 3d-cubic pore structure and/or bigger pore size. The present invention is corroborated by in vivo data in an example of the use of the drug delivery vehicles disclosed here, showing enhancements of solubility in an actual pharmaceutical context, that is: enhancements of solubility of anti-retroviral ATV co-administered with proton pump inhibitors.

The present invention also relates to cosmetic active ingredients such as poorly soluble vitamins. Vitamins are essential nutrients that the human body needs in small amounts for various roles. Vitamins are divided into two groups: water-soluble (B-complex and C) and fat-soluble (A, D, E and K). Unlike water-soluble vitamins that need regular replacement in the body, fat-soluble vitamins are stored in the liver and fatty tissues, and are eliminated much more slowly than water-soluble vitamins.

Vitamin A, also called retinol, has many functions in the body. In addition to helping the eyes adjust to light changes, vitamin A plays an important role in bone growth, tooth development, reproduction, cell division and gene expression. Also, the skin, eyes and mucous membranes of the mouth, nose, throat and lungs depend on vitamin A to remain moist.

Retinol, along with other retinoids, has enjoyed increasing popularity as an active ingredient in skin care compositions, especially for acne, photoaging, and sun damage. However, more so than other retinoids, retinol tends to decompose on exposure to light, heat and oxygen. The problem of decomposition has been addressed to some extent by formulating retinol with antioxidants and chelating agents, and storing it in opaque or colored containers, and several patents and published applications describe water-in-oil emulsions containing retinol.

Softgel formulations have recently become of greater interest in the formulation of products for topical applications to the skin, because the softgel provide an attractive single us method for dispensing the product. However, it is well known that unmodified softgels are incompatible with water, and that typical emulsions, whether water-in-oil, will degrade the gelatin shell of a softgel. U.S. Pat. No. 5,587,149 discloses a softgel formulation for water soluble active ingredients, such as ascorbic acid (Vitamin C), where the fill material comprises an emulsion of which a first phase includes polyethylene glycol (into which the water-soluble active ingredients is dissolved and the second phase includes a silicone fluid). U.S. Pat. No. 4,826,828 reports a water-oil type emulsion wherein retinol, retinyl acetate and retynil palmitate are stabilized by an antioxidant such as BHT (butylated hydroxytoluene), or BHA (butylated hydroxytoluene). U.S. Pat. No. 4,720,353 reports a water-in-oil type emulsion wherein retinol is also stabilized with BHA, ascorbic acid or tocopherol.

EP 0440398 reports an oil-in-water type emulsion wherein retinol is stabilized with one or more kinds of water soluble antioxidants or chelating agents to improve chemical stability of retinol.

In the previous examples, the inventors refer to stabilizing retinol or retinoids, wherein antioxidants and chelating agents are the active elements. However the only difference between formulations or patented methodologies is the kind of chelating agents and properties of antioxidants used, so with these methods, the solubility of retinol remains poor as well as retinol keeps unprotected from factors such as oxygen, moisture or light. The present invention results in enhancements of solubility and stability of poorly soluble cosmetic actives, exemplified by Retinol.

BRIEF DESCRIPTION OF THE INVENTION

The present invention provides a pharmaceutical or cosmetic formulation which utilizes a nanoporous folic acid materials and other nanoporous silica materials as the delivery vehicle for the poorly water-soluble drugs, and the formulations are prepared by methods of wet impregnation technique, rotary evaporation technique, co-spray drying techniques or freeze-drying technique.

In particular, the present invention also provides a pharmaceutical or cosmetic formulation which comprises a nanoporous composition with the ordered and uniform pore size produced by using folic acid as pore template; a water-insoluble active ingredient included inside or/and outside of the mesoporous particles; and a precipitation inhibitor to stabilize the super-saturating condition.

An amorphous active ingredient is confined inside the nanoscale channels with a thermodynamic stable state for periods longer than 1 year. The smaller the pore space the API is confined in, i.e. the larger the nanoconfinement, the easier to dissolve the poorly water-soluble drugs in aqueous medium is. The nanoporous folic acid composition applied in the invention possess smaller pores than other mesoporous or nanoporous materials described elsewhere, and this is important to it's improved behavior in comparison to other formulations including porous materials. The nanoconfinement referred to in the present invention is described by the following equation, where by d* represents the minimum pore space necessary to create a non-crystalline amorphous state of the drug within a nanopore:

$$d^* = 4\sigma_{cl} T_m^\infty / ((T_m^\infty - T) \Delta H_m \rho_c)$$

where $\sigma_{cl}$ is the surface energy between crystal and melt, $\Delta H_m$ is the heat of melting, $T_m^\infty$ is the bulk melting temperature and $\rho_c$ the crystal density. Below the critical diameter d*, the surface energy contributions are larger than the energetic gain upon crystallization. Additionally to this thermodynamic concern, nanoconfinement will decrease the crystallization kinetics of the compound through a dispersion of nucleation sites within the porous structure and an immobilization of crystallization "nutrients" within the nanopores is achieved. These effects are increased drastically the lower the pore size.

The present invention provides a novel formulation and methods to improve the dissolution and enhance the solubility of poorly water-soluble ingredients, particularly for pharmaceutical active compounds that are not suitable for oral administration or that violate at least one of Lipinskis Rule-of-5.

A substantially poorly water-soluble active ingredient could be selected from a member of antifungal, analgesic, anti-cholesterol, cholesterol-reducing, anti-pyretic, anti-inflammatory, antimicrobial, decongestant, antihistamine, HMG-CoA reductase inhibitors, antiretroviral drug, and cancer drugs.

SUMMARY OF THE INVENTION

The present invention relates to a pharmaceutical or cosmetic composition, comprising:
- a substantially poorly water-soluble pharmaceutical or cosmetic active ingredient; and
- a nanoporous folic acid material, wherein the active pharmaceutical ingredient is incorporated inside the nanoporous channels of the particles.

In an embodiment of the present invention, said substantially poorly water-soluble pharmaceutical active ingredients is composed of one or more species selected from the group of: antifungal agents, analgesic agents, cholesterol absorption inhibitors, anti-pyretics, anti-inflammatory, decongestants, antihistamine, antiretroviral drugs, and cancer drugs: as defined in the detailed descriptions of the invention.

In a further embodiment of the present invention, said substantially poorly water-soluble cosmetic active ingredients is composed of one or several from the group of fat-soluble vitamins and pro-vitamins and stabilized vitamins and stabilized provitamins.

Preferably, said poorly water-soluble pharmaceutical active ingredient is present at about 0.1 wt % to 90 wt %, and preferably between 15-55 wt % of the total weight of the nanoporous material.

In particular, said poorly water-soluble compounds are active ingredients with solubility <10 g/L and preferably <1 g/L in water at 25° C., or by having partition constants above 2, or by violating at least one of Lipinski's rule-of-5.

In a preferred embodiment, said nanoporous silica materials are manufactured by a method as descibed in the international patent application WO 2009/101110 A2, whose description is incorporated herein by reference.

Preferably, the particle size of said nanoporous materials is in the range between 50 nm to 100 μm.

Preferably, the said pore size of said nanoporous materials is between 1 nm to 50 nm.

The pore volume of said nanoporous materials is preferably about 0.2 $cm^3/g$ to 2 $cm^3/g$.

Preferably, said nanoporous materials is present at about 1 wt % to 90 wt %, and more preably preferably between 40-80 wt %.

In a particular embodiment of the present invention, the pharmaceutical and cosmetic composition comprises an additional precipitation inhibitor such as polymer, surfactant and cyclodextrin, as better defined in the detailed description of the invention, which is present in the range of 0.1 wt % to 50 wt % of the total weight of the nanoporous material in the formulation.

In a further embodiment of the present invention, the pharmaceutical and cosmetic composition comprises a proton pump inhibitor of the group: Omeprazole, Lansoprazole, Dexlansoprazole Esomeprazole, Pantoprazole, Rabeprazole and Revaprazan, present in a concentration, between 1-50 wt % of the total nanoporous material in the formulation.

In a further embodiment of the present invention, said active pharmaceutical compound is Atazanivir and/or its bisulphate analogue.

In a further aspect, the present invention relates to a super-saturating delivery system comprising a pharmaceutical or cosmetic composition as defined above having an enhancement in solubility in water, compared to the pharmaceutical or cosmetic composition without said nanoporous composition.

Also, the present invention relates to a super-saturating delivery system comprising a pharmaceutical or cosmetic composition as defined above having an enhancement in stability, compared to the pharmaceutical or cosmetic composition without said nanoporous composition.

Furthermore, the present invention relates to a super-saturating delivery system comprising a pharmaceutical or cosmetic composition as defined above having an enhancement in bioavailability in vivo, compared to the pharmaceutical composition without said nanoporous composition, in particular which is between 2-100 times higher, at pHs between 1.8-8.

A further aspect of the present invention relates to a method for preparing a pharmaceutical or cosmetic composition sa defined above, said method comprising wet impregnation technique, rotary evaporation technique, co-spray drying techniques or freeze-drying technique.

Preferably said wet impregnation technique comprises: adding an amount of the nanoporous materials to a solution of the pharmaceutical or cosmetic active ingredients, and making the nanoporous materials entrap the said active ingredients in the nanopores through capillary action upon evaporation of the solvent.

Said co-spray drying technique preferably comprises: dissolving a poorly water-soluble pharmaceutical or cosmetic active ingredient in organic solvent such as ethanol, methanol, and acetone, an in general in suitable solvents or co-solvents including $C_1$-$C_6$ alkanols, ketones, esters, ethers, aliphatic hydrocarbons, aromatic hydrocabons, halogenated solvents, cycloaliphatic solvents, aromatic heterocyclic solvents, and mixtures thereof.

DETAILED DESCRIPTION OF THE INVENTION

Nanoporous materials in the invention are manufactured by a method as described in the international patent application WO 2009/101110 A2, whose description is incorporated herein by reference.

For the purposes of the present invention, the term "poorly water-soluble drugs" and "poorly water-soluble active ingredients" define active pharmaceutical or cosmetic ingredients with a solubility <10 g/L and preferably <1 g/L in aqueous medium (at 25° C.). Additionally they can be defined by having several, 1 or more violations of Lipinski's Rule-of-5.

The super-saturation solution is defined so that the concentration induced by the pharmaceutical or cosmetic formulation is higher than the equilibrium concentration induced by the pharmaceutical crystals.

Poorly Water-Soluble Pharmaceutical and Cosmetic Active Ingredients

All substantially poorly water-soluble active ingredients are suitable for use the nanoporous materials to obtain the supersaturation state. These active ingredients include antifungal agents, analgesic agents, cholesterol absorption inhibitors, anti-pyretics, anti-inflammatory, decongestants, antihistamine, antiretroviral drugs, and cancer drugs, and derivatives of these compounds.

Examples of antifungal are: Ergosterol inhibitors, e.g., Bifonazole, Clomidazole, Clotrimazole, Croconazole, Econazole, Fenticonazole, Ketoconazole, Isoconazole, Miconazole, Neticonazole, Oxiconazole, Sertaconazole, Sulconazole, Tioconazole, Fluconazole, Fosfluconazole, Fluconazole, Itraconazole, Posaconazole, Voriconazole, Thiabendazole, Natamycin, Nystatin, Amphotericin B, Amorolfine, Butenafine, Naftifine, Terbinafine, Terbinafine, β-glucan synthase inhibitors, such as echinocandins (Anidulafungin, Caspofungin, Micafungin), Thymidylate synthase inhibitors Flucytosine, Mitotic inhibitors Griseofulvin, and the others such as Bromochlorosalicylanilide, Methylrosaniline, Tribromometacresol, Undecylenic acid, Polynoxylin, Chlorophetanol, Chlorphenesin, Ticlatone, Sulbentine, Ethyl hydroxybenzoate, Haloprogin, Ciclopirox, Amorolfine, Tolnaftate, Tolciclate.

Examples of analgesics are: Codeine, Morphine, Acetyldihydrocodeine, Benzylmorphine, Buprenorphine, Desomorphine, Dihydrocodeine, Dihydromorphine, Ethylmorphine, Diamorphine, Hydrocodone, Hydromorphinol, Hydromorphone, Nicocodeine, Nicodicodeine, Nicomorphine, Oxycodone, Oxymorphone, Alphaprodine, Anileridine, Butorphanol, Dextromoramide, Dextropropoxyphene, Dezocine, Fentanyl, Ketobemidone, Levorphanol, Methadone, Meptazinol, Nalbuphine, Pentazocine, Propoxyphene, Propiram, Pethidine, Phenazocine, Piminodine, Piritramide, Tapentadol, Tilidine, Tramadol, Ajulemic acid, AM404, Cannabis, Nabilone, Nabiximols, Tetrahydrocannabinol, Paracetamol (acetaminophen), Phenacetin, Propacetamol, Fenoprofen, Flurbiprofen, Ibuprofen, Ketoprofen, Naproxen, Oxaprozin, Meloxicam, Piroxicam, Diclofenac, Indometacin, Ketorolac, Nabumetone, Sulindac, Tolmetin, Celecoxib, Rofecoxib, Valdecoxib, Parecoxib, Lumiracoxib, Amitryptiline, Befiradol, Bicifadine, Carisoprodol, Camphor, Clonidine, Cyclobenzaprine, Duloxetine, Esreboxetine, Flupirtine, Gabapentin, Glafenine, Hydroxyzine, Ketamine, Menthol, Nefopam, Orphenadrine, Pregabalin, Scopolamine, Tebanicline, Trazodone, Ziconotide, Aspirin, Benorylate, Diflunisal, Ethenzamide, Magnesium salicylate, Salicin, Salicylamide, Salsalate, Trisalate, Wintergreen.

Examples of cholesterol absorption inhibitors are: Ezetimibe, SCH-48461, Cholestyramine, Colestipol, Colestilan, Colextran, Colesevelam, Simvastatin, Atorvastatin, Fluvastatin, Lovastatin, Mevastatin, Pitavastatin, Pravastatin, Rosuvastatin, Cerivastatin, Niceritrol, Nicofuranose, Nicotinyl alcohol, Clofibrate, Bezafibrate, Aluminium clofibrate, Fenofibrate, Simfibrate, Ronifibrate, Ciprofibrate, Etofibrate, Clofibride, Clinofibrate, Anacetrapib, Torcetrapib, JTT-705, Dextrothyroxine, Probucol, Tiadenol, Benfluorex, Omega-3-triglycerides, Magnesium pyridoxal 5-phosphate glutamate, Policosanol, Lapaquistat, Alipogene tiparvovec.

Examples of anti-pyretics are: Metamizole, Nabumetone, Nimesulide, Phenazone, Quinine. Examples of anti-inflammatory are: Ampyrone, Clofezone, Kebuzone, Mofebutazone, Oxyphenbutazone, Phenylbutazone, Sulfinpyrazone, Feprazone, Aceclofenac, Acemetacin, Alclofenac, Bromfenac, Bumadizone, Bufexamac, Difenpiramide, Etodolac, Fentiazac, Lonazolac, Oxametacin, Proglumetacin, Zomepirac, Amfenac, Ampiroxicam, Droxicam, Lornoxicam, Tenoxicam, Alminoprofen, Benoxaprofen, Dexibuprofen, Dexketoprofen, Fenbufen, Flurbiprofen, Ibuproxam, Indoprofen, Pirprofen, Suprofen, Tiaprofenic acid, Flufenamic acid, Meclofenamic acid, Tolfenamic acid, Niflumic acid, Morniflumate, Azapropazone, Etoricoxib, Glucosamine, Benzydamine, Glycosaminoglycan, Proquazone, Superoxide dismutase/Orgotein, Diacerein, Tenidap, Oxaceprol, Chondroitin sulfate.

Examples of decongestants are: Ephedrine, Levo-methamphetamine, Naphazoline, Oxymetazoline, Phenylephrine, Phenylpropanolamine, Propylhexedrine, Pseudoephedrine, Synephrine, Tetrahydrozoline, Cafaminol, Cyclopentamine, Epinephrine, Fenoxazoline, Levonordefrin, Mephentermine, Metizoline, Norepinephrine, Tramazoline, Tuaminoheptane, Tymazoline.

Examples of antihistamine are: $H_1$ agonists such as HTMT, UR-AK49; $H_1$ antagonists such as: 1st generation: 4-Methyldiphenhydramine, Alimemazine, Antazoline, Azatadine, Bamipine, Benzatropine (Benztropine), Bepotastine, Bromazine, Brompheniramine, Buclizine, Captodiame, Carbinoxamine, Chlorcyclizine, Chloropyramine, Chlorothen, Chlorpheniramine, Chlorphenoxamine, Cinnarizine, Clemastine, Clobenzepam, Clocinizine, Cyclizine, Cyproheptadine, Dacemazine, Deptropine, Dexbrompheniramine, Dexchlorpheniramine, Dimenhydrinate, Dimetindene, Diphenhydramine, Diphenylpyraline, Doxylamine, Embramine, Etybenzatropine (Ethylbenztropine), Etymemazine, Histapyrrodine, Homochlorcyclizine, Hydroxyethylpromethazine, Hydroxyzine, Isopromethazine, Isothipendyl, Meclizine, Mepyramine (Pyrilamine), Mequitazine, Methafurylene, Methapyrilene, Methdilazine, Moxastine, Niaprazine, Orphenadrine, Oxatomide, Oxomemazine, Phenindamine, Pheniramine, Phenyltoloxamine, Pimethixene, Piperoxan, Promethazine, Propiomazine, Pyrrobutamine, Talastine, Thenalidine, Thenyldiamine, Thiazinamium, Thonzylamine, Tolpropamine, Tripelennamine, Triprolidine; 2nd generation: Acrivastine, Astemizole, Azelastine, Cetirizine, Clemizole, Clobenztropine, Ebastine, Emedastine, Epinastine, Ketotifen, Latrepirdine, Levocabastine, Loratadine, Mebhydrolin, Mizolastine, Olopatadine, Rupatadine, Setastine, Terfenadine; 3rd generation: Desloratadine, Fexofenadine, Levocetirizine; Miscellaneous: Tricyclic Antidepressants (Amitriptyline, Doxepin, Trimipramine, etc), Tetracyclic Antidepressants (Mianserin, Mirtazapine, etc), Serotonin Antagonists and Reuptake Inhibitors (Trazodone, Nefazodone), Typical Antipsychotics (Chlorpromazine, Thioridazine, etc), Atypical Antipsychotics (Clozapine, Olanzapine, Quetiapine, etc). $H_2$ Agonists: Amthamine, Betazole, Dimaprit, Histamine, HTMT, Impromidine, UR-AK49; $H_2$ Antagonists: Cimetidine, Famotidine, Lafutidine, Lavoltidine, Metiamide, Niperotidine, Nizatidine, Ranitidine, Roxatidine; $H_3$ Agonists: α-Methylhistamine, Cipralisant, Histamine, Imetit, Immepip, Immethridine, Methimepip, Proxyfan; $H_3$ Antagonists: A-349,821, A-423,579, ABT-239, Betahistine, Burimamide, Ciproxifan, Clobenpropit, Conessine, GSK-189,254, Impentamine, Iodophenpropit, JNJ-5,207,852, MK-0249, NNC-38-1,049, PF-03654746, SCH-79,687, Thioperamide, Tiprolisant, VUF-5,681; $H_4$ Agonists: 4-Methylhistamine, Histamine, VUF-8,430; $H_4$ Antagonists: JNJ-7,777,120, Thioperamide, VUF-6,002. VMAT inhibitors: Ibogaine, Reserpine, Tetrabenazine; HDC inhibitors: α-FMH, Brocresine, Catechin, Cyanidanol-3, McN-A-1293, ME, Meciadanol, Naringenin, Thiazol-4-ylmethoxyamine, Tritoqualine, Zy-15,029; HNMT inhibitors: Amodiaquine, BW-301U, Diphenhydramine, Harmaline, Metoprine, Quinacrine, SKF-91,488, Tacrine; DAO inhibitors: 1,4-Diamino-2-butyne, Aminoguanidine; the others: L-Histidine and Vitamin B6.

Examples of antiretroviral drugs are: Saquinavir, Ritonavir, Indinavir, Nelfinavir, Amprenavir, Lopinavir, Atazanavir, Fosamprenavir, Tipranavir, Darunavir.

Other examples of orally administered agents are melphalan, busulfan, capecitabine. Examples of poorly soluble cosmetic ingredients are: fat soluble vitamins (A, D, E and K), pro-vitamins, and commercially available stabilized forms of fat-soluble vitamins such as Retinol 50C.

Pharmaceutical Excipients as Stabilizers of Supersaturation.

Supersaturation is a thermodynamically unstable condition and the driving force for precipitation. In order to take advantage of the creation of intraluminal supersaturation, this state should be stabilized for a time period allowing sufficient transepithelial transport by temporary inhibiting precipitation. Different classes of excipients have been investigated as precipitation inhibitors.

It is well known that polymers stabilize supersaturation state. Examples include cellulose derivatives such as Methyl cellulose, Ethyl cellulose, Hydroxyethyl cellulose, Hydroxypropyl cellulose, Hydroxyethyl methylcellulose, Hydroxypropyl methyl cellulose, Carboxymethyl cellulose et al.; vinyl polymers such as Polyvinyl alcohol, polyvinylpyrrolodone, poly(vinylpyrrolidone-co-vinyl acetate) et al.; and ethylene polymers like PEG.

Surfactants also delay precipitation from supersaturated solutions. When surfactants are added to a supersaturated solution at concentrations exceeding their critical micelle concentration, an increase in drug solubility will reduce the rate of nucleation and crystal growth. Examples include TPGS, Tween® 20, Crenophor® RH40 et al.

Similar to surfactants, cyclodextrins are well known for their stabilizing capability and capacity. The present invention does not exclude the co-formulation of these together with the nanoporous formulation and pharmaceutical compound.

Incorporation Methods of Pharmaceutical and Cosmetic Active Agents.

Although the pharmaceutical active ingredients disclosed in the current document are poorly soluble in aqueous medium, they behave very differently owing to their different structural formulae. For example, some of them have pH-dependent solubility in aqueous medium, some of them are soluble in polar solvents, and some of them are soluble in non-polar solvents. Therefore, the present invention provides versatile methods for different pharmaceutical active ingredients, irrespective of their physicochemical properties.

The present invention discloses a method to load a wetness-impregnation method for loading pharmaceutical compound using solvents that may solubilize them. Thus the drug compound must be soluble in at least one solvent, be it polar or non-polar. For example, the pH-dependent soluble drugs can be incorporated in acid solution by wet impregnation technique. The final solid dispersion comprises on a weight basis (percent by weight) 1 wt % to 55 wt % of active ingredient and preferably between 15-55 wt %.

In a certain embodiment of the present invention the poorly water-soluble pharmaceutical active ingredients are incorporated in the channels of nanoporous materials by rotary evaporation the suitable active ingredient solution with nanoporous materials in vacuum. The final composition of the solid dispersion could be about 0.1 wt % to 90 wt % of active ingredients by weight percent, and preferably between 15-55 wt %.

The present invention provides also the co-spray drying technique which is implemented by dissolving a poorly water-soluble drug in organic solvent such as ethanol, methanol, and acetone. Other suitable solvents or co-solvents include $C_1$-$C_6$ alkanols, ketones, esters, ethers, aliphatic hydrocarbons, aromatic hydrocabons, halogenated solvents, cycloaliphatic solvents, aromatic heterocyclic solvents, and mixtures thereof. The nanoporous materials are added in the solution with stirring for sufficient time to make the active ingredients incorporated in the nanoporous channels.

In some aspects, the active ingredients are sensitive to the temperature and oxygen, so the present invention provides freeze drying technique. Freeze-drying causes less damage to the substance than other dehydration methods using higher temperatures. Freeze-drying does not usually cause shrinkage or toughening of the material being dried. The formulation including active substance, nanoporous materials and precipitant inhibitors can be prepared by a process of freeze drying technique.

Additional Excipients

The pharmaceutical or cosmetic formulations according to the invention may in addition contain as further constituents conventional pharmaceutical auxiliary substances such as suitable filler, binder, disintegrants, lubricants, glidants, swellable erodible hydrophilic materials, insoluble edible materials, taste-masking and odor-masking.

Mechanism of Action

The present invention is consistent with a model of suppression of crystallization due to the pore size of the nanoporous materials of the present invention being below a certain critical diameter d*, as described above. Both surface energy and thermodynamic considerations suppress crystallization of the pharmaceutical compound within the nanopores and reduce the overall energetic barriers for solubility of the compound achieving a supersaturation state. The pharmacokinetic rates of release that can be achieved are consistent with both Higuchi-models and power-law models of release, depending on the drug compound used.

EXAMPLES

Example 1—Incorporation and Release of Atazanavir In Vitro

Three nanoporous materials with the different pore size were chosen as models to test the loading and release properties of poorly water-soluble drugs. STA-11 and AMS-6 with the Ia3d cubic pore structures and NFM-1 with the hexagonal pore structure were applied in the report, and all of them are calcined samples.

Atazanavir, ATV is a protease inhibitor antiretroviral used for the treatment of infection by the human immunodeficiency virus (HIV). Worldwide, over 40 million people are infected with the human immunodeficiency virus (HIV). The high activity antiretroviral therapy (HAART) combines at least three antiretroviral drugs and has been used to extend the lifespan of the HIV-infected patients. Chronic intake of HAART is mandatory to control HIV infection. The frequent administration of several drugs in relatively high doses is a main cause of patient non-compliance and a hurdle toward the fulfilment of the pharmacotherapy. Atzanivir is a lipophilic drug compound with log P=5.20. Despite a value of 4 violations of Lipinski's Rule-of-5, it's bioavailability is of between 60-68% and half-life of 6.5 hours. However, the bioavailability of ATV is severely hampered, as much as 78% reduction in plasma concentration (Cmin), when this is co-administered with proton pump inhibitors leading to a significant decrease in its effectiveness.

Rotary evaporating method has been applied to incorporated atazanavir by using methanol as solvent, since the solubility is pretty low aqueous medium even in acid condition whilst atazanavir can dissolve in methanol freely. The procedure is given below: a high concentrated drug solution was prepared in the methanol, following by adding three different nanoporous silica into the drug-methanol solution. The mixture was stirred for 2 hours in room temperature for sufficient incorporation. Finally, the loaded nanoporous silica samples were evaporated by rotary evaporator in vacuum, and dried in the air. The loading amount is 28.6% for all the samples, which is calculated by the adding amount of atazanavir in proportional to the amount of mesoporous silica samples.

FIG. 1 (left) shows the kinetic release profile of crystal atazanavir and atazanavir in three different nanoporous silica materials. FIG. 1 (right) shows Maximum solubility of ATV released from mesoporous silica compared with the solubility of free crystalline atazanavir in SIF after 4 hours.

In order to compare the concentrations of atazanavir crystallite and atazanavir in nanoporous silica, the UV absorbance scans of atazanavir in SIF with the time are shown in FIG. 1. The solubility of ATV does not increase with time and the solubility is very low; however, the solubility of the atazanavir in three different nanoporous silica not only is many times higher than the free drug, but also increases much with the time. The atazanavir super-saturating solutions from the nanoporous silica. The drug in NFM-1 nanoporous silica with the smallest pore size (2.3 nm) shows the highest solubility; however STA-11 with the largest pore size (6 nm) shows the lowest enhancement in solubility among the three nanoporous silica materials owing to its lowest nanoconfinement effect over the API. Particularly, the super-saturating state produced from NFM-1 could be maintain for 24 hours, and the other two could maintain for 7 hours.

For nanoporous material NFM-1 loaded with ATV, the dissolution rate appears to decrease with increased particle concentration as a percentage of loaded amount. However, the actual solubility (see FIG. 2: (a) Dissolution curves of free atazanavir and loaded ATV simulated Intestine fluid (SIF); (b) Dissolution curves for free and loaded NFM-1-ATV with varied particle/SIF ratio as a percentage of solubilized ATV; and (c) as compound concentration) shows that higher concentration of NFM-1-ATV particles provide a higher solubility, whereby the maximum solubility reached 18 mg/L after 4 hours, in comparison to 0.254 mg/L after a similar time for the free ATV. Hence the present invention delivers an approximate enhancement in solubility of 71 times. In the case of the highest particle concentration, a supersaturation state is maintained for 4 hours after which the dissolution decreases rapidly due to crystallization of the drug in the water bath in which the dissolution study is conducted.

Example 2—The Amorphous State of ATV in Nanoporous Materials

In order to show the amorphous state of ATV in nanoporous materials, FIG. 3 reports the High angle X-ray diffraction patterns of free atazanavir (ATV), STA-11-ATV, AMS-6-ATV and NFM-1-ATV, recorded after a period of 1.5 years showing the amorphous nature of the ATV within the nanoporous materials in the present invention.

Example 3—Incorporation and Release of Dasatinib

Dasatinib is an anti-cancer drug which is an oral dual BCR/ABL and Src family tyrosine kinases inhibitor approved for use in patients with chronic myelogenous leukemia (CML) after imatinib treatment and Philadelphia chromosome-positive acute lymphoblastic leukemia (Ph+ ALL). The drug is a pH-dependent soluble in aqueous medium, which has the biggest solubility when the pH value is 2.6. Therefore, glycine/HCl buffer with the pH value of 2.6 is applied for the incorporation of dasatinib. This buffer is not toxic and less adsorption competent capability than drug.

The TG-DTA data of dasatinib in three different nanoporous silica are shown in FIG. 4. STA-11 samples adsorbed very few amount of glycine from the buffer as shown in the blank test. There is one big peak between 200° C. and 500° C. which was assigned to the burning of drugs as shown in the DTA profiles of mesoporous silica with the loading dasatinib. The peak above 500° C. is considered as the condensation of the hydroxyl groups on the mesoporous silica surface.

As for Dasatinib, the 1st loading amount of drugs is about 21% in STA-11 with the biggest pore size. However, the loading amount of dasatinib did not show big differences within three mesoporous silica with the different pore size and structure. Also the present invention could provide the $2^{nd}$ and $3^{rd}$ loading for higher loading amount.

The kinetic release profiles of dasatinib in three different mesoporous silica are shown in FIG. 5. As for release of dasatinib in SGF, only about 90% of drugs are released from the mesoporous silica, and all of them have very fast release in the beginning. Dasatinib is susceptible to acid-alkali hydrolysis and oxidation. [Stability Indicating HPTLC and LC Determination of Dasatinib in Pharmaceutical Dosage Form, Chromatographia, 2007, 66, 95-102] The simulated gastric fluid is very acid condition with the pH value of 1.2. The solubility of Dasatinib is higher, so there is no clear solubility enhancement of Dasatinib in mesoporous silica because they release very fast. 90% of dasatinib only was released out maybe because dasatinib was degraded with the loading process in acid solution with the pH value of 2.6. As for release property of dasatinib in SIF, 90% dasatinib in STA-11 and NFM-1 were released out within two and half hours, which means all of the loaded dasatinib released out, so dasatinib in STA-11 and NFM-1 release faster than crystal dasatinib from this point. However, Dasatinib in AMS-6 were released slower and some of dasatinib can not be released out, maybe because of the 3-D pore structure and smaller pore size.

Example 4—Incorporation and Release of Ketoconazole

Ketoconazole is a synthetic broad-spectrum antifungal agent, which is also poorly water-soluble drug. Ketoconazole has the very similar solubility properties with dasatinib, therefore, the same incorporation method as dasatinib is applying for ketoconazole.

The TG-DTA data of ketoconazole in three different mesoporous silica are shown in FIG. 6. The releases of ketoconazole in three different mesoporous silica in SIF are faster than crystal ketoconazole as shown in FIG. 7. The released drugs from STA-11 and NFM-1 show higher solubility in the beginning than the drugs released from AMS-6. STA-11 is 3-D pore structure, however bigger pore size about 6 nm, so the drug are easily going in or out, and although NFM-1 samples have smaller pore size with 2-3 nm, the hexagonal 2-D channels also are easier for the loading and releasing of drugs. The concentration of the released drug decreasing after 10 hours is due to recrystallization of the drug due to the conditions (sink conditions) in which the experiment is conducted.

Example 5—In Vivo Enhancement in Bioavailability of ATV Co-Administered with Proton Pump (H+)-Inhibitors Proton pump ($H^+$) inhibitors are used by HIV patients to treat the symptoms of heartburn and stomach pains which are common secondary effects after HIV medication. The origin of this decrease in bioavailability of antiretroviral drugs is caused by the precipitation of the drug under neutral conditions, and its reduced solubility. Hence the development of a formulation capable of maintaining high bioavailability when ATV is co-administered with $H^+$-inhibitors is likely to lead to a considerable improvement in patient comfort as well as effectiveness of the treatment for patients with HIV. The following example illustrates how the current invention tackles this problem through an acceleration of dissolution rate and the stability of supersaturation of pharmaceutical active ATV when the drug is encapsulated through simple procedures within nanoporous silica materials of different as those disclosed in the claims. An in vivo pharmacokinetic study was conducted in order to validate the enhancement in dissolution observed for ATV with nanoporous material NFM-1, in the context with co-administration with ($H^+$)-inhibitors, for the best performing mesoporous silica NFM-1. A single oral administration at one dose to three female Sprague Dawley rats was given after approximately 5 hours of administration with (H+)-inhibitors Omeoprazole. Administrations was performed using overnight fasted animals. Blood samples were collected in EDTA tubes at six different time points, i.e. 0.5 hours, 1 hour, 2 hours, 4 hours, 8 hours and 24 hours after administration, and blood plasma concentrations of ATV were determined via HPLC-MS. The pharmacokinetic profile of whole blood plasma ATV concentration for NFM-1-ATV administered rats in comparison to free ATV administered rats is shown in FIG. 8. A very pronounced improvement in ATV absorption is observed during the first hour of the study. FIG. 8 shows the pharmacokinetic profile for ATV in whole blood samples for NFM-1-ATV and free ATV administered Sprague Dawley rats, in the presence of proton pump inhibitor omeprazole. Mean±standard deviation. N=3 animals per time point.

Example 6—Loading and Release of Retinol 50C in Nanoporous Silica

As a mesoporous silica material, AMS-6 was selected in this example, having an Ia3d cubic pore structures, and a small pore diameter (around 4 nm average). Prior to the loading, AMS-6 was thermally treated in order to increase the hydrophobic of the inner/outer surface. 10 grams of calcined AMS-6 were placed in an oven and heated at 600° C. during 12 hours. The selected active ingredient was Retinol 50C. Retinol 50C is a formulation comprising pure Retinol and an excipient namely Polisorbate 20 used as stabilizer. The appearance is yellow oil, non soluble in water but soluble in organic solvents such as alcohols, ketones, among others. The percentage of each component in the formulation is 50% in weight.

For the loading, 10 g of Retinol 50C were dissolved in 500 ml of methanol (MeOH) at room temperature. The solution was stirred for 2 hours. Then, 10 g of calcined AMS-6, previously thermally treated were added into the Retinol 50C/MeOH solution, and stirred for 2 hours. All the mixture was transferred to a rotovapor, and the solvent was extracted under stirring, vacuum and hot temperature (around 60 degrees). The loaded material, named AMS6/Ret50C, were extracted from the round flask and dried on air.

The loading effectiveness was tested by Themogravimetric Analysis (TGA). FIGS. 9 and 10 show the TGA of both Retinol 50C and AMS6/Ret50C. The decomposition of Retinol 50C is clearly evidenced at a range of temperature between 200 and 600 degrees, which implies the two components of the formulation Retinol and Polisorbate 20C (See FIG. 9). In the TGA of the loaded material AMS6/Ret50C, a very similar pattern is observed, which indicates that both components Retinol and Polisorbate were either introduced into the silica channels or anchored in the external surface of the silica particles. The final composition of the new formulation exhibited a 63% in weight of loaded Retino150C into AMS-6.

Figure 1:
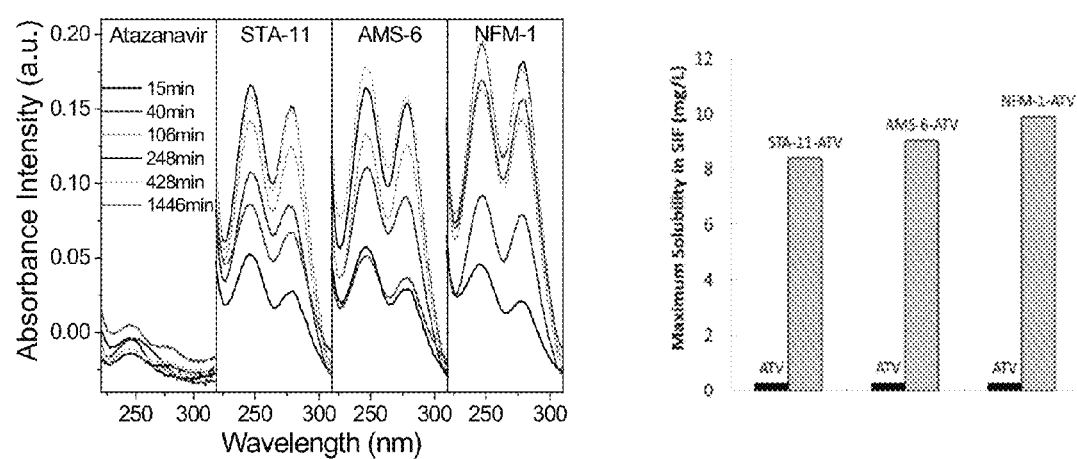
Figure 2:
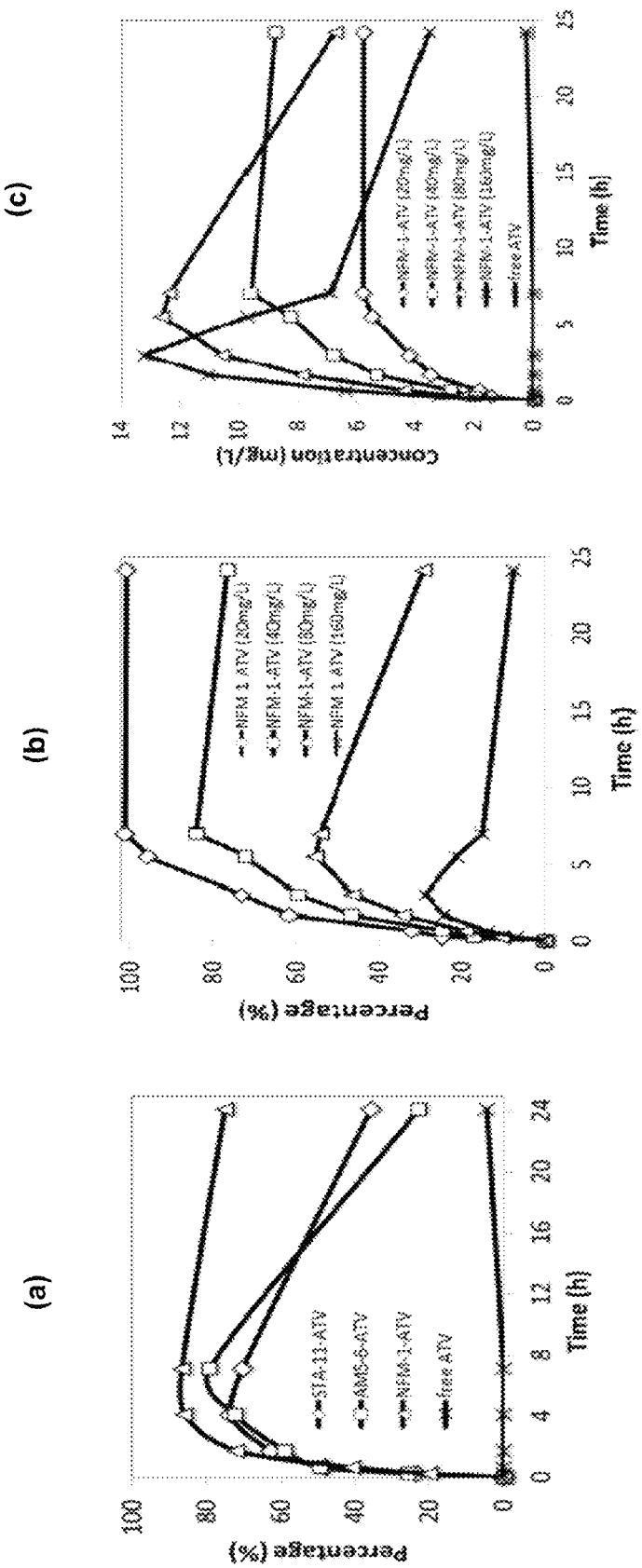
Figure 3:
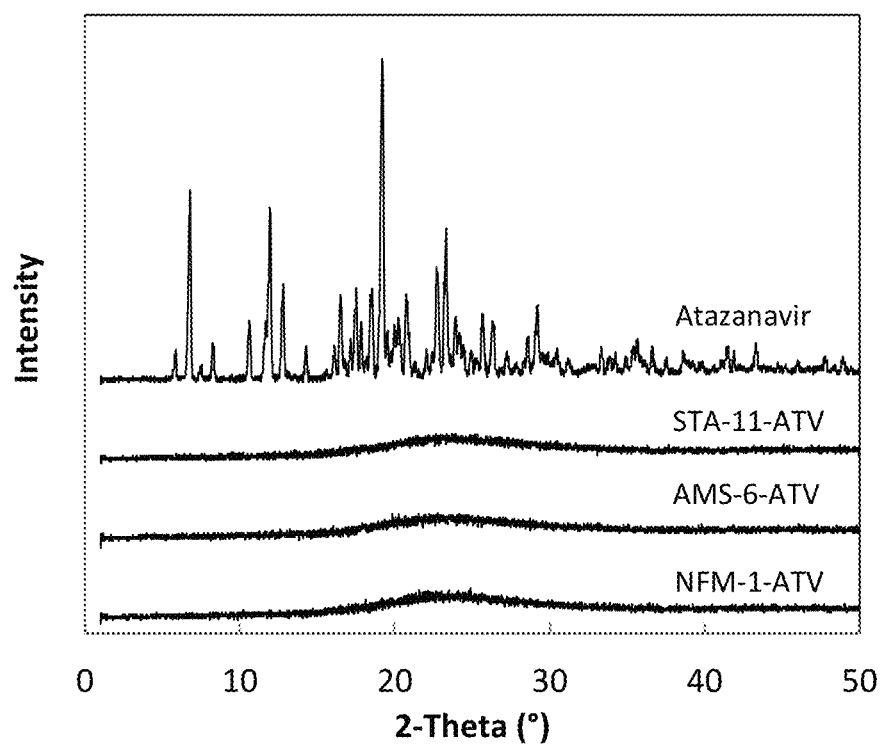
Figure 4:
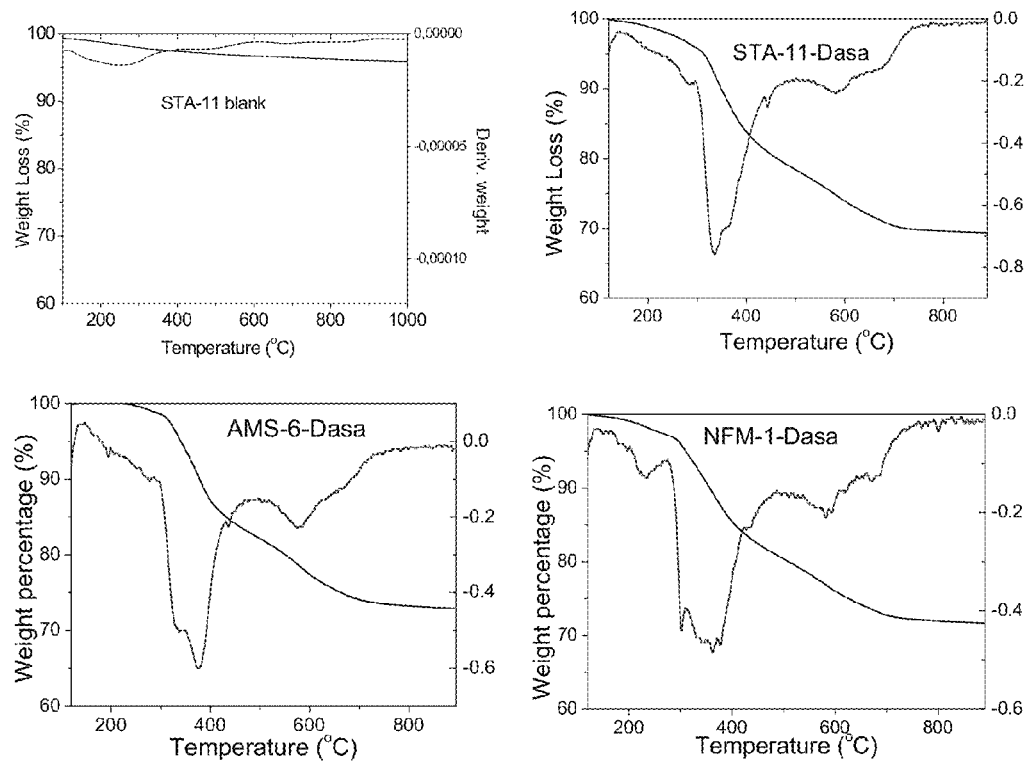
Figure 5:
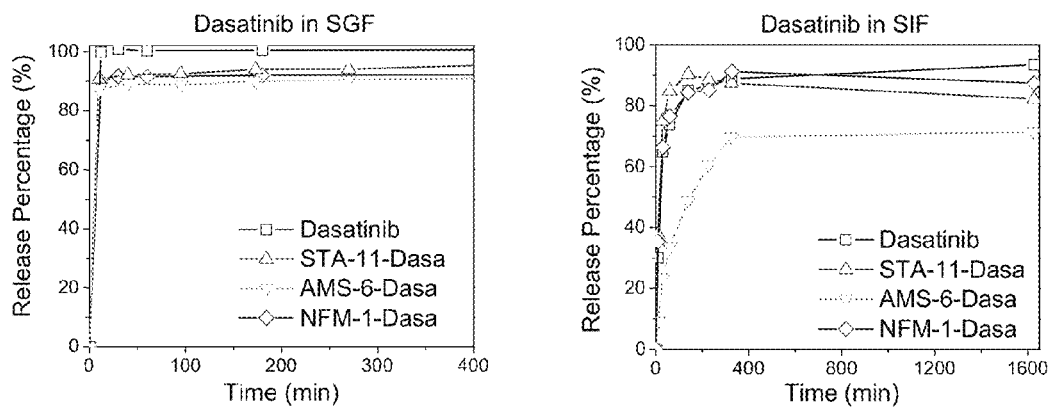
Figure 6:
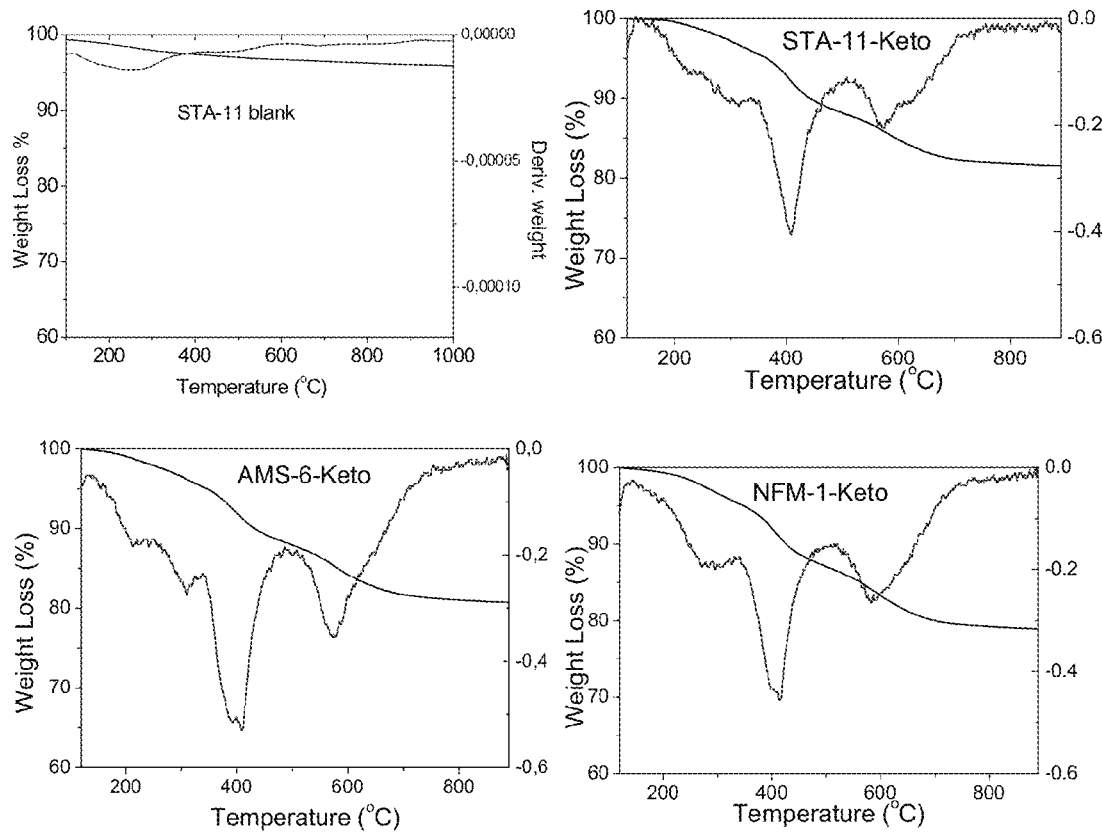
Figure 7:
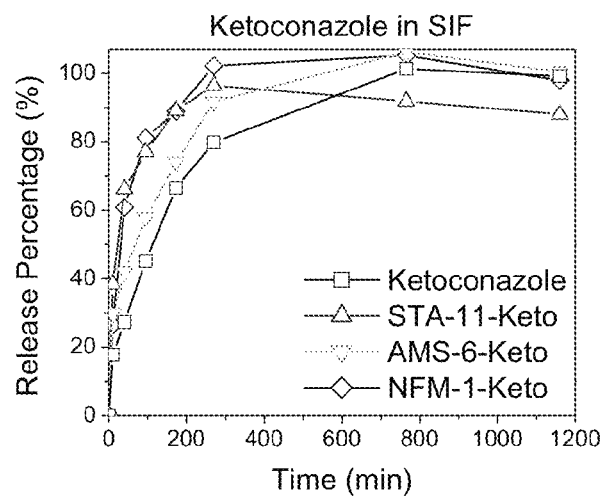
Figure 8:
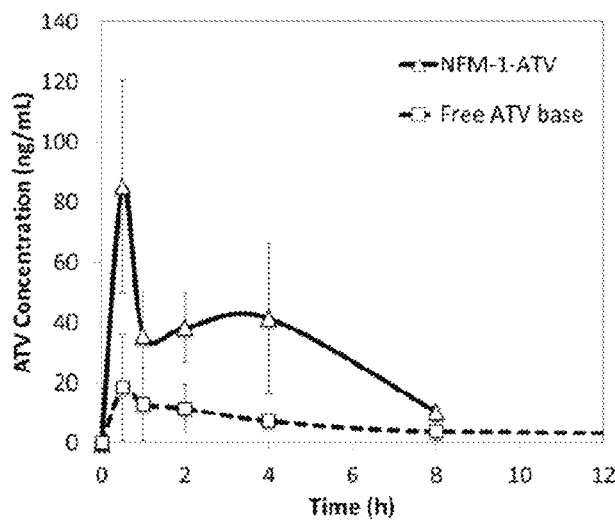
Figure 9:
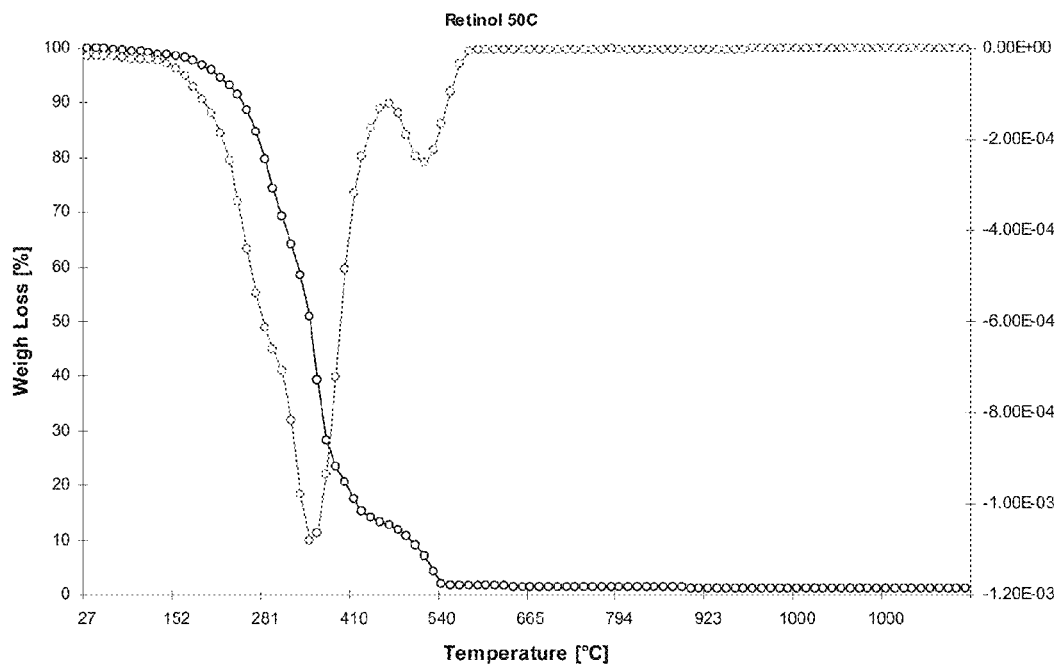
Figure 10:
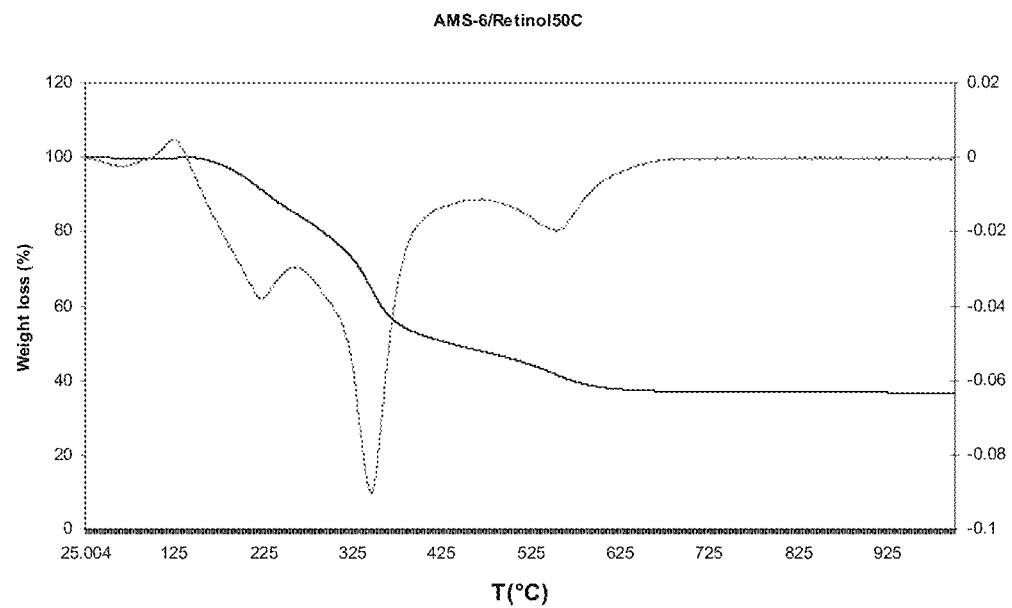
Figure 11:
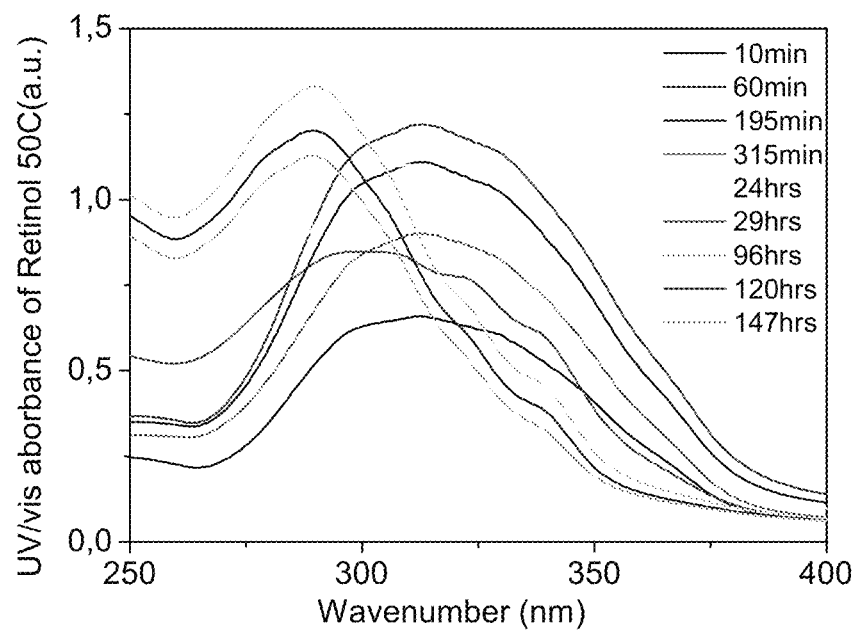
FIG. 11 shows the kinetic release profiles of 100 mg Retinol 50C in 500 ml water at 37° C. under speed stirring of 150 rpm.
Figure 12:
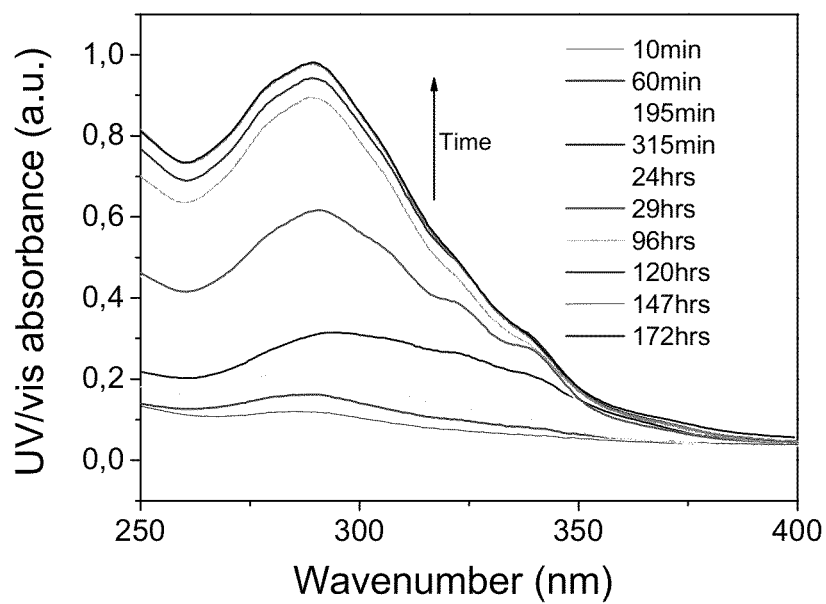
FIG. 12 shows the kinetic release profiles of 100 mg AMS6/Ret50C in 500 ml water at 37° C. under speed stirring of 150 rpm.
Figure 13:
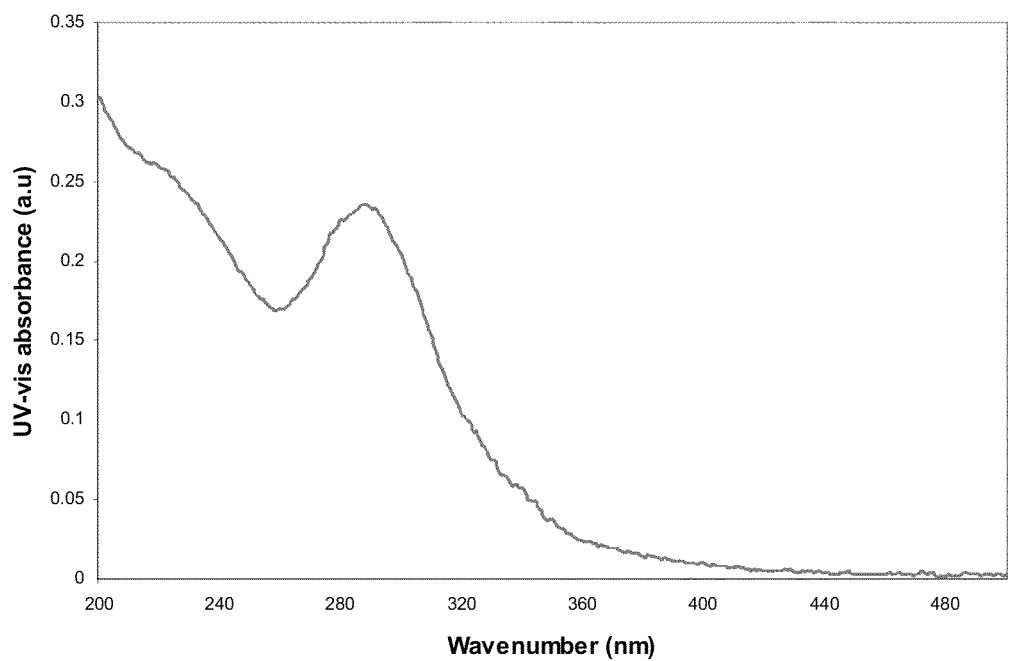
FIG. 13 shows the UV-VIS spectrum of a dissolution of Retinol in water (conc. 3.4 mg/L), at 37° C. under speed stirring of 150 rpm, recorded after 20 days release from a nanoporous material.

The invention claimed is:

1. A pharmaceutical or cosmetic composition, comprising:
   an amorphous substantially poorly water-soluble pharmaceutical or cosmetic active ingredient, achieving a supersaturation state within a nanoporous particle; and
   a nanoporous material with an ordered and uniform pore size produced by using folic acid as a pore template, wherein the nanoporous material has a pore size in the range between 1 nm to 50 nm, and wherein the nanoporous material has a pore volume from 0.2 $cm^3/g$ to 2 $cm^3/g$, and wherein the amorphous substantially poorly water-soluble pharmaceutical or cosmetic active ingredient is contained in a nanoporous channel of the nanoporous particle in a supersaturation state after synthesis of the nanoporous particle, and wherein the amorphous substantially poorly water-soluble pharmaceutical or cosmetic active ingredient has a solubility less than 10 g/L in water at 25° C. or has a partition coefficient greater than 2 or violates at least one of Lipinski's rule-of 5, and has an enhanced solubility rate and faster dissolution rate as compared to said pharmaceutical or cosmetic active ingredient that is not contained in the nanoporous channel of the nanoporous particle.

2. The composition of claim 1, wherein said amorphous substantially poorly water-soluble pharmaceutical active ingredient is composed of one or more species selected from the group of: antifungal agents, analgesic agents, cholesterol absorption inhibitors, anti-pyretics, anti-inflammatory, decongestants, antihistamine, antiretroviral drugs, and cancer drugs.

3. The composition of claim 1, wherein said amorphous substantially poorly water-soluble cosmetic active ingredient is composed of one or more species selected from the group of: fat-soluble vitamins and pro-vitamins and stabilized vitamins and stabilized provitamins.

4. The composition of claim 1, wherein said amorphous poorly water-soluble pharmaceutical or cosmetic active ingredient is present at about 0.1 wt % to 90 wt % of the total weight of the nanoporous material.

5. The composition of claim 1, wherein the particle size of said nanoporous material is in the range between 50 nm to 100 µm.

6. The composition of claim 1, further comprising a precipitation inhibitor which is present in the range of 0.1 wt % to 50 wt % of the total weight of the nanoporous material in the formulation.

7. The composition of claim 1, wherein said amorphous substantially poorly water-soluble pharmaceutical active ingredient comprises a proton pump inhibitor of the group: Omeprazole, Lansoprazole, Dexlansoprazole Esomeprazole, Pantoprazole, Rabeprazole and Revaprazan, in a concentration, between 1-50 wt % of the total nanoporous material in the formulation.

8. The composition of claim 1, wherein said amorphous substantially poorly water-soluble pharmaceutical active ingredient comprises Atazanavir and/or its bisulphate analogue.

9. The composition of claim 2, wherein said amorphous poorly water-soluble pharmaceutical or cosmetic active ingredient is present at about 0.1 wt % to 90 wt % of the total weight of the nanoporous material.

10. The composition of claim 3, wherein said amorphous substantially poorly water-soluble pharmaceutical or cosmetic active ingredient is present at about 0.1 wt % to 90 wt % of the total weight of the nanoporous material.

11. The composition of claim 1, wherein said amorphous substantially poorly water-soluble pharmaceutical or cosmetic active ingredient is present between 0.1 wt %-90 wt % of the total weight of the nanoporous material.

12. The composition of claim 11, wherein said amorphous substantially poorly water-soluble pharmaceutical or cosmetic active ingredient is present between 15-55 wt % of the total weight of the nanoporous material.

13. The composition according to claim 1, wherein said super-saturation state is achieved using a wet impregnation technique, rotary evaporation technique, co-spray drying technique or freeze-drying technique.

14. The composition according to claim 1, wherein said super-saturation state is achieved using the wet impregnation technique.

15. The composition according to claim 1, wherein said super-saturation state is achieved using the rotary evaporation technique.

16. The composition according to claim 1, wherein said super-saturation state is achieved using the co-spray drying technique.

17. The composition according to claim 1, wherein said super-saturation state is achieved using the freeze-drying technique.

18. A method for preparing a pharmaceutical or cosmetic composition according to claim 1, said method comprising wet impregnation technique, rotary evaporation technique, co-spray drying techniques or freeze-drying technique.

19. The method according to claim 18, wherein said wet impregnation technique comprises: adding an amount of the nanoporous materials to a solution of the pharmaceutical or cosmetic active ingredients, and making the nanoporous materials entrap the said active ingredients in the nanopores through capillary action upon evaporation of the solvent.

20. The method according to claim 18, wherein said co-spray drying technique comprises: dissolving a poorly water-soluble pharmaceutical or cosmetic active ingredient in organic solvent such as ethanol, methanol, and acetone, an in general in suitable solvents or co-solvents including $C_1$-$C_6$ alkanols, ketones, esters, ethers, aliphatic hydrocarbons, aromatic hydrocarbons, halogenated solvents, cycloaliphatic solvents, aromatic heterocyclic solvents, and mixtures thereof.

* * * * *